(12) United States Patent
Okuyama (10) Patent No.: US 10,357,655 B2
(45) Date of Patent: Jul. 23, 2019

(54) FREQUENCY-DEPENDENT FOCUSING SYSTEMS AND METHODS FOR USE IN A COCHLEAR IMPLANT SYSTEM

(71) Applicant: ADVANCED BIONICS AG, Staefa (CH)

(72) Inventor: Nobutaka Okuyama, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 622 days.

(21) Appl. No.: 14/909,971

(22) PCT Filed: Aug. 13, 2013

(86) PCT No.: PCT/US2013/054770
§ 371 (c)(1),
(2) Date: Feb. 3, 2016

(87) PCT Pub. No.: WO2015/023267
PCT Pub. Date: Feb. 19, 2015

(65) Prior Publication Data
US 2016/0184586 A1    Jun. 30, 2016

(51) Int. Cl.
*A61N 1/36* (2006.01)
*H04M 1/725* (2006.01)
(Continued)

(52) U.S. Cl.
CPC ....... *A61N 1/36036* (2017.08); *A61N 1/0541* (2013.01); *A61N 1/36038* (2017.08); *A61N 1/36039* (2017.08); *H04R 25/50* (2013.01)

(58) Field of Classification Search
CPC ............ A61N 1/36032; A61N 1/36036; A61N 1/0541; A61N 1/36038; A61N 1/36039; H03G 3/20; H04R 25/50
(Continued)

(56) References Cited

U.S. PATENT DOCUMENTS 7,110,821 B1    9/2006  Ross
2009/0264960 A1*  10/2009  Litvak ................ A61N 1/36036
                                                       607/57
(Continued)

OTHER PUBLICATIONS

International Search Report and Written Opinion received in International Application No. PCT/US13/054770, dated Dec. 5, 2013.

*Primary Examiner* — Christopher Koharski
*Assistant Examiner* — Pamela M. Bays
(74) *Attorney, Agent, or Firm* — ALG Intellectual Property, LLC (57) ABSTRACT

An exemplary system includes a processing facility and a control facility. The processing facility is configured to 1) divide an audio signal presented to a cochlear implant patient into a plurality of analysis channels each containing a frequency domain signal, and 2) maintain data representative of a crossover frequency. The control facility is configured to 1) direct a cochlear implant to apply electrical stimulation representative of each frequency domain signal included in a plurality of low frequency analysis channels located below the crossover frequency in accordance with a low frequency stimulation strategy that includes a degree of focusing, and 2) direct the cochlear implant to apply electrical stimulation representative of each frequency domain signal included in a plurality of high frequency analysis channels located above the crossover frequency in accordance with a high frequency stimulation strategy that includes a lesser degree of focusing than the low frequency stimulation strategy.

19 Claims, 10 Drawing Sheets

(51) Int. Cl.
*H04R 29/00* (2006.01)
*A61N 1/05* (2006.01)
*H04R 25/00* (2006.01)

(58) Field of Classification Search
USPC .......................................................... 607/57
See application file for complete search history.

(56) References Cited

U.S. PATENT DOCUMENTS

2011/0064241 A1   3/2011  Kulkarni et al.
2011/0077710 A1*  3/2011  Saoji ................. A61N 1/36036
                                                         607/57
2012/0243715 A1*  9/2012  Pedersen ............. H04R 25/505
                                                         381/316

* cited by examiner

FREQUENCY-DEPENDENT FOCUSING SYSTEMS AND METHODS FOR USE IN A COCHLEAR IMPLANT SYSTEM

BACKGROUND INFORMATION

Current steering is often used in cochlear implant systems to more effectively represent sound presented to cochlear implant patients. In traditional current steering strategies, weighted stimulation current is applied concurrently to two adjacent electrodes by a cochlear implant system in order to stimulate a stimulation site located in between areas associated with the electrodes. In this manner, the cochlear implant system may create a perception of a frequency in between the frequencies associated with the electrodes.

While current steering is effective in augmenting sound perception, it may introduce spectral broadening, which in turn may compromise spectral resolution. This may be particularly problematic in cases where an audio signal (e.g., speech) includes spectral peaks that represent the distinguishing or meaningful frequency components of the audio signal. In these cases, it may be desirable to present electrical stimulation representative of the spectral peaks to a cochlear implant patient in as fine of spectral resolution as possible.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Frequency-dependent focusing systems and methods for use in a cochlear implant system are described herein. As will be described below, a sound processor included in a cochlear implant system may 1) divide an audio signal presented to a cochlear implant patient into a plurality of analysis channels each containing a frequency domain signal representative of a distinct frequency portion of the audio signal, 2) maintain data representative of a crossover frequency associated with the patient, the crossover frequency representing a boundary between a plurality of low frequency analysis channels included in the plurality of analysis channels and a plurality of high frequency analysis channels included in the plurality of analysis channels, 3) direct a cochlear implant associated with the patient to apply electrical stimulation representative of each frequency domain signal included in the plurality of low frequency analysis channels located below the crossover frequency in accordance with a low frequency stimulation strategy that includes a degree of focusing, and 4) direct the cochlear implant to apply electrical stimulation representative of each frequency domain signal included in the plurality of high frequency analysis channels located above the crossover frequency in accordance with a high frequency stimulation strategy that includes a lesser degree of focusing than the low frequency stimulation strategy.

As used herein, a stimulation strategy that includes "focusing" refers to a stimulation strategy that directs a cochlear implant to apply compensating current to one or more compensating electrodes while main current representative of a portion of an audio signal is applied to one or more main electrodes. As will be described below, the compensating current is opposite in phase compared to the main current and serves to focus (e.g., narrow) the excitation field produced by the main current, thereby resulting in finer spectral resolution compared to stimulation strategies in which focusing is not used. Focusing may also be referred to as "spectral focusing."

By using relatively more focusing in low frequency bands (i.e., frequency bands located below the crossover frequency) than in high frequency bands (i.e., frequency bands located above the crossover frequency), the systems and methods described herein may preserve or enhance frequency resolution of the low frequency components included in an audio signal presented to a cochlear implant patient. This may result in improved perception by the cochlear implant patient of the audio signal, especially in cases where the audio signal includes speech, music, and/or other types of acoustic content that have spectral peaks (e.g., formants) primarily located in the low frequency bands. Moreover, by using relatively less focusing (e.g., no focusing) in the high frequency bands, the systems and methods described herein may serve to minimize perception by the user of undesirable content (e.g., harmonics and ambient noise) typically present in the high frequency bands and minimize power consumption by the cochlear implant system.

Figure 1:
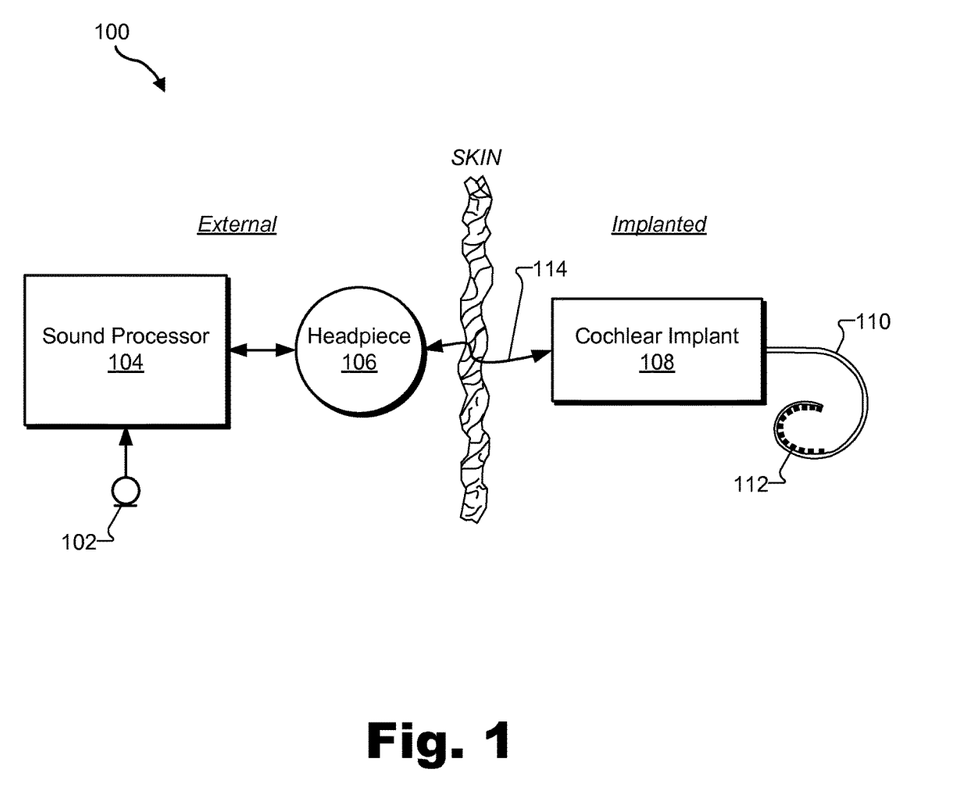
FIG. 1 illustrates an exemplary cochlear implant system according to principles described herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
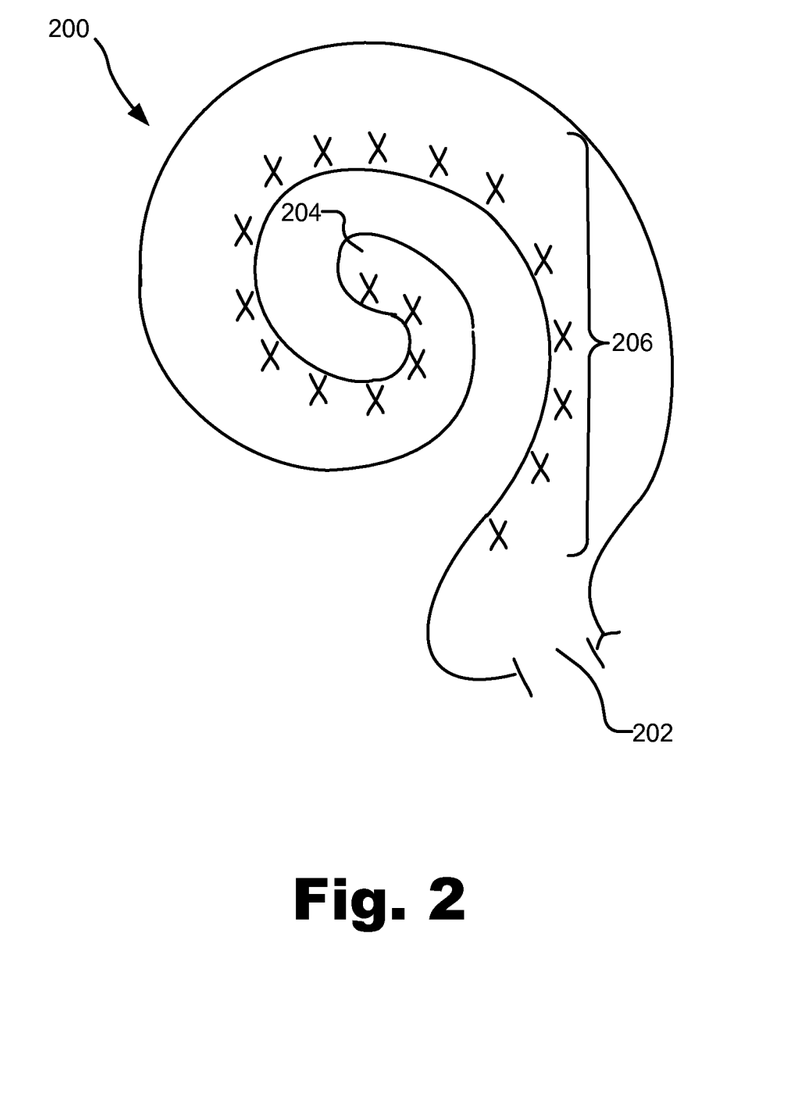
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
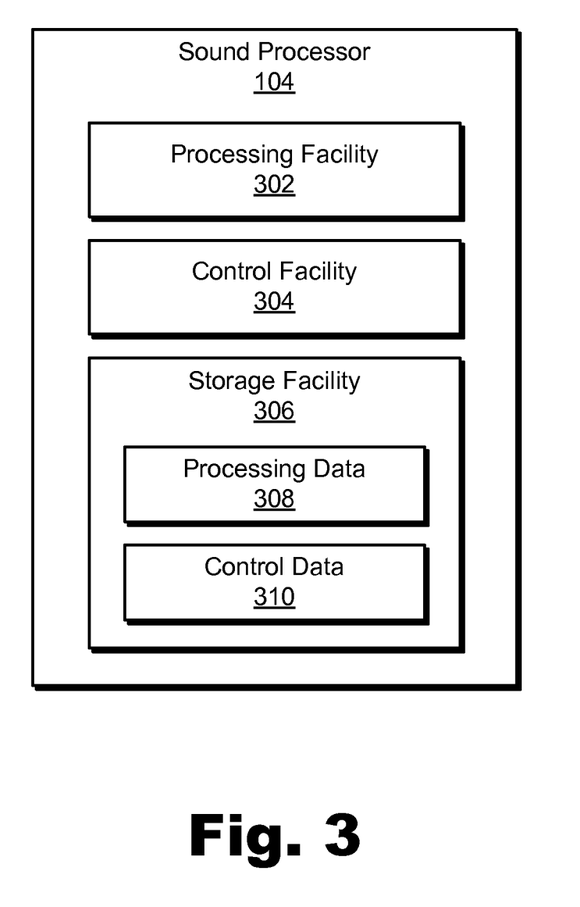
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a processing facility 302, a control facility 304, and a storage facility 306, which may be in communication with one another using any suitable communication technologies. Storage facility 306 may be configured to maintain processing data 308 generated and/or used by processing facility 302, and control data 310 (e.g., data representative of one or more stimulation parameters) generated and/or used by control facility 304. Storage facility 306 may maintain additional or alternative data as may serve a particular implementation. One or more of facilities 302-306 may include a computing device or processor configured to perform one or more of the functions described herein. Facilities 302-306 will now be described in more detail.

Processing facility 302 may be configured to process an audio signal presented to a cochlear implant patient (e.g., an audio signal detected by microphone 102, an audio signal input by way of an auxiliary audio input port, etc.). For example, processing facility 302 may perform one or more pre-processing operations, spectral analysis operations, noise reduction operations, mapping operations, and/or any other types of signal processing operations on a detected audio signal as may serve a particular application.

In some examples, processing facility 302 may divide an audio signal presented to a cochlear implant patient into a plurality of analysis channels each containing a frequency domain signal (or simply "signal") representative of a distinct frequency portion of the audio signal. This may be performed in any suitable manner. For example, processing facility 302 may be implemented by a plurality of band-pass filters configured to divide the audio signal into a plurality of frequency channels or bands. Additionally or alternatively, processing facility 302 may be configured to convert the audio signal from a time domain into a frequency domain and then divide the resulting frequency bins into the plurality of analysis channels. To this end, processing facility 302 may include one or more components configured to apply a Discrete Fourier Transform (e.g., a Fast Fourier Transform ("FFT")) to the audio signal.

Figure 4:
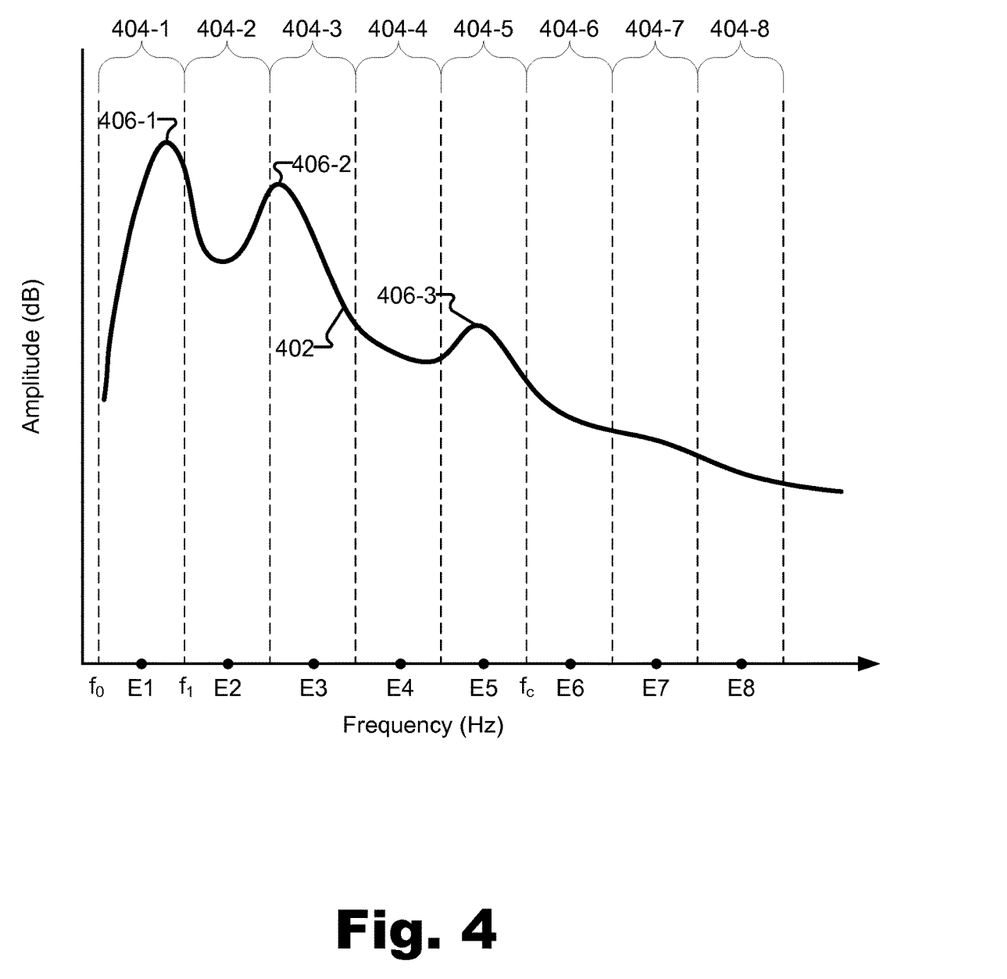
FIG. 4 shows an exemplary frequency domain representation of an audio signal that may be presented to a cochlear implant patient according to principles described herein.

To illustrate, FIG. 4 shows an exemplary frequency domain representation of an audio signal 402 that may be presented to a cochlear implant patient. As illustrated by the dashed vertical lines, processing facility 302 has divided the audio signal 402 into a plurality of analysis channels 404-1 through 404-8 (collectively "analysis channels 404"). Each analysis channel 404 corresponds to a particular frequency band. For example, analysis channel 404-1 corresponds to a frequency band defined by frequencies $f_0$ and $f_1$. While eight analysis channels 404 are shown in FIG. 4, it will be recognized that processing facility 302 may divide the audio signal 402 into any number of analysis channels as may serve a particular application.

As shown in FIG. 4, each analysis channel 404 may be associated with an electrode (e.g., one of electrodes E1 through E8) disposed within a cochlea of the patient. For example, FIG. 4 shows that analysis channel 404-1 is associated with electrode E1. In other words, electrode E1 is located at a position within the cochlea that corresponds to the frequency band associated with analysis channel 404-1. In some examples, multiple electrodes are associated with a particular analysis channel 404-1. For example, in cases where current steering between two electrodes is used to represent an audio signal, the two electrodes may be associated with the analysis channel and located at positions that correspond to the frequency boundaries of the frequency band associated with the analysis channel.

As shown in FIG. 4, each analysis channel 404 may contain a frequency domain signal representative of a distinct frequency portion of audio signal 402. For example, the portion of audio signal 402 that is included in the frequency band defined by frequencies $f_0$ and $f_1$ may be referred to as the frequency domain signal contained within analysis channel 404-1.

Processing facility 302 may be further configured to maintain data representative of a crossover frequency associated with the cochlear implant patient. As used herein, a "crossover frequency" represents a boundary between relatively low frequency bands and relatively high frequency bands. Analysis channels that correspond to the relatively low frequency bands are referred to herein as "low frequency analysis channels." Likewise, analysis channels that correspond to the relatively high frequency bands are referred to herein as "high frequency analysis channels." For example, with respect to FIG. 4, the crossover frequency is represented by $f_c$. Hence, analysis channels 404-1 through 404-5 are low frequency analysis channels and analysis channels 404-6 through 404-8 are high frequency analysis channels.

As illustrated in FIG. 4, various spectral peaks 406 (e.g., spectral peaks 406-1 through 406-3) may be located within one or more of the low frequency analysis channels 404-1 through 404-5. As described above, these spectral peaks 406 may represent the distinguishing or meaningful frequency components of audio signal 402. For example, if audio signal 402 includes speech, spectral peaks 406 may be representative of formants included in the speech. As used herein, a formant represents a resonance of the human vocal tract and is associated with the utterance of a vowel sound.

As illustrated in FIG. 4, formants and other types of spectral peaks are typically located in the low frequency analysis channels (e.g., below 2100 Hz). Hence, by using a relatively high degree of focusing to represent the frequency domain signals included in the low frequency analysis channels, spectral peaks 406 may be represented more precisely, thereby reducing spectral smearing and improving recognition of the information (e.g., a vowel sound) represented by the spectral peaks 406 by the cochlear implant patient.

The crossover frequency that represents the boundary between the low frequency analysis channels and the high frequency analysis channels may be determined in any suitable manner. For example, the crossover frequency may be automatically set to a predetermined value (e.g., 2100 Hz) regardless of the characteristics of the patient.

Alternatively, the crossover frequency may be set depending on one or more physiological characteristics of the patient. For example, the crossover frequency may be set based on a patient's age, gender, weight, size, and/or any other physiological characteristic of the patient as may serve a particular implementation.

In some examples, processing facility 302 may determine the crossover frequency in accordance with a fitting procedure performed with respect to the patient. For example, a fitting system may present tonal components to a patient starting at a low frequency and sweeping through to a high frequency. The fitting system may measure an ability of the patient to perceive the tonal components and, based on this measurement, determine the crossover frequency.

In some examples, processing facility 302 may maintain data representative of a plurality of different crossover frequencies each associated with a particular audio signal classification. Processing facility 302 may then classify an incoming audio signal and determine the crossover frequency that is to be associated with the audio signal based on the classification of the audio signal.

For example, different types of audio signals (e.g., speech, music, noise, etc.) may result in spectral peaks being located within different analysis channels. Hence, it may be desirable to adjust the crossover frequency based on the type of audio signal being presented to the patient. To this end, processing facility 302 may classify an audio signal as being of a certain type and accordingly use a crossover frequency associated with that type of audio signal as the crossover frequency that defines which analysis channels are low frequency analysis channels and which analysis channels are high frequency analysis channels.

Returning to FIG. 3, control facility 304 may be configured to control an operation of cochlear implant 108. For example, with respect to the example shown in FIG. 4, control facility 304 may direct cochlear implant 108 to apply electrical stimulation representative of each frequency domain signal included in low frequency analysis channels 404-1 through 404-5 in accordance with a low frequency stimulation strategy that includes a degree of focusing. Control facility 304 may also direct cochlear implant 108 to apply electrical stimulation representative of each frequency domain signal included in high frequency analysis channels 404-6 through 404-8 in accordance with a high frequency stimulation strategy that includes a lesser degree of focusing than the low frequency stimulation strategy.

Figure 5:
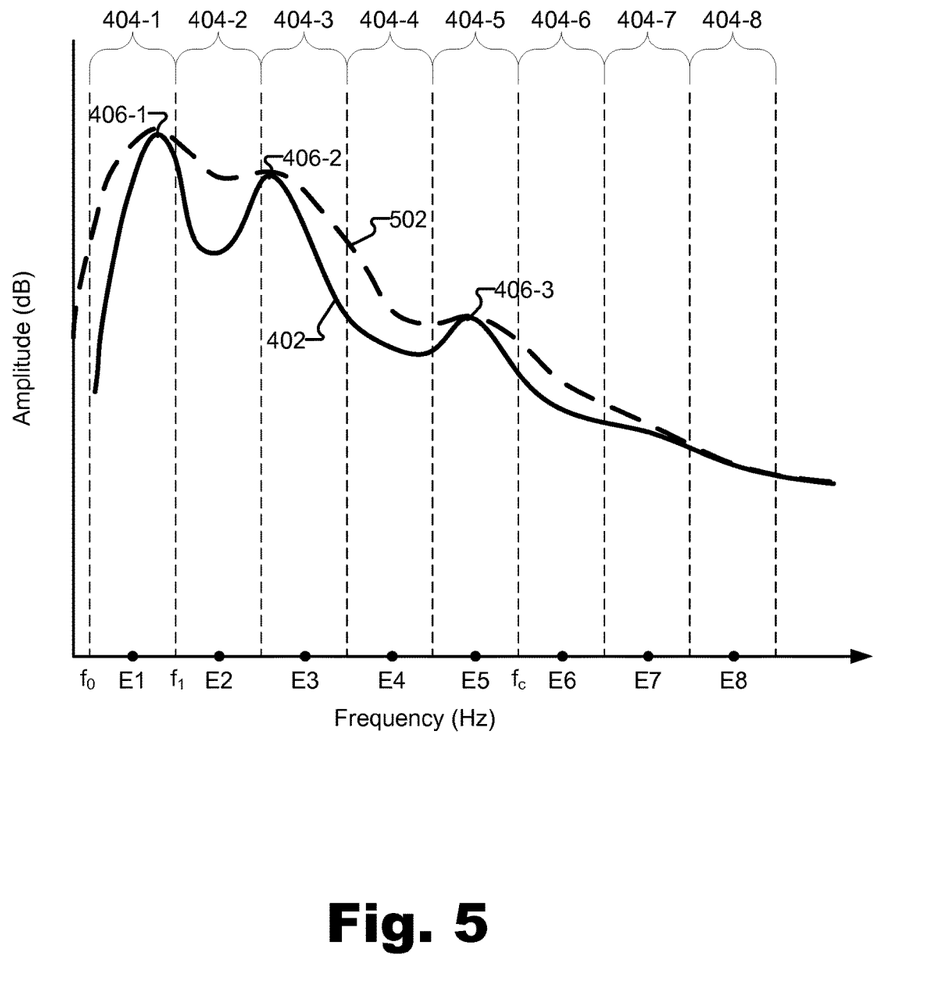
FIG. 5 shows a frequency response that may be produced as a result of a stimulation strategy that does not include any degree of focusing according to principles described herein.

Reference is now made to FIG. 5. FIG. 5 shows the same frequency domain representation of audio signal 402 illustrated in FIG. 4. FIG. 5 also shows a frequency response 502 (as captured by a short term frequency transform ("STFT")) of the audio signal 402 that may be produced as a result of a stimulation strategy that does not include any degree of focusing. As shown, frequency response 502 is spectrally smeared. As a result, spectral peaks 406 may not be readily discernable by the patient. However, by using a stimulation strategy that includes focusing to represent the frequency domain signals included in the low frequency analysis channels, finer spectral resolution may be achieved, thereby resulting in improved perception by the cochlear implant patient of the information represented by spectral peaks 406.

Control facility 304 may direct cochlear implant 108 to apply electrical stimulation representative of a frequency domain signal included in a particular low frequency analysis channel in accordance with a low frequency stimulation strategy that includes focusing in any suitable manner. For example, control facility 304 may direct cochlear implant 108 to concurrently apply a main current to at least one main electrode associated with a low frequency analysis channel and a compensating current to two or more compensating electrodes associated with the low frequency analysis channel. The compensating current is opposite in phase compared to the main current in order to focus the excitation field created by the main current.

Figure 6:
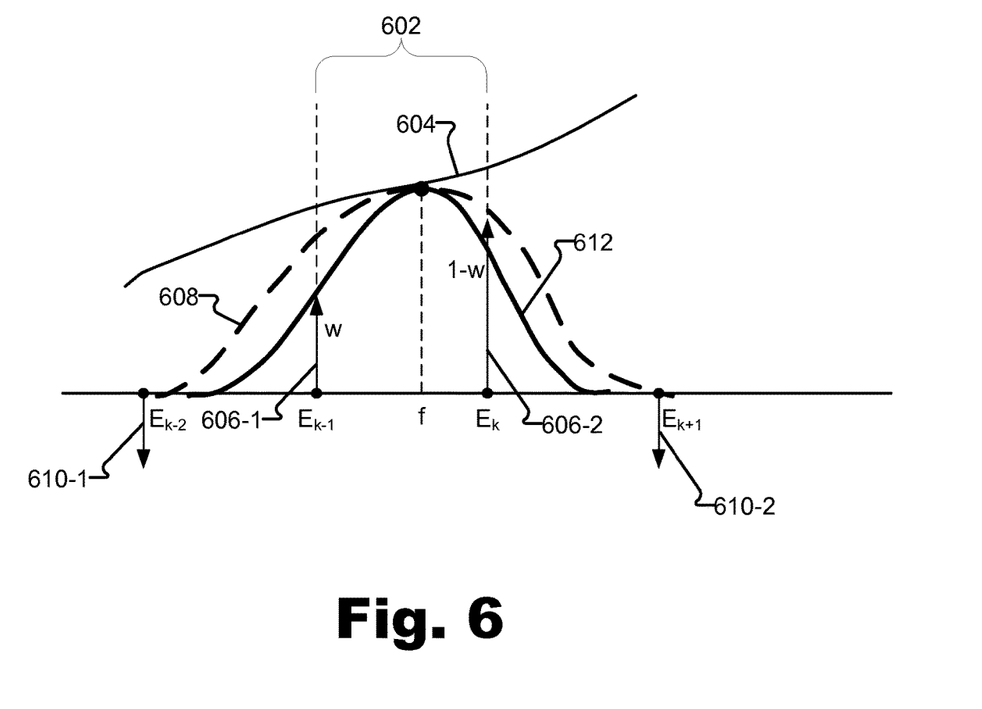
FIG. 6 shows an exemplary analysis channel according to principles described herein.

To illustrate, FIG. 6 shows an exemplary analysis channel 602 (which may be either a high or low frequency analysis channel) that contains a frequency domain signal 604. In the example of FIG. 6, analysis channel 602 corresponds to a frequency band associated with two electrodes $E_{k-1}$ and $E_k$. In this configuration, current steering between electrodes $E_{k-1}$ and $E_k$ may be used to represent frequency domain signal 604.

To illustrate, FIG. 6 shows that main current 606-1 having a weighted amplitude of w and main current 606-2 having a weighted amplitude of 1-w are concurrently applied to electrodes $E_{k-1}$ and $E_k$, respectively. This results in a peak envelope located at frequency f. In the absence of focusing (i.e., if no compensating current is applied to one or more electrodes surrounding electrodes $E_{k-1}$ and $E_k$), the excitation field associated with the peak envelope is relatively broad, as represented by envelope 608.

However, in accordance with a stimulation strategy that includes focusing, compensating current 610-1 and 610-2 (collectively "compensating current 610") opposite in polarity compared to that of main current 606-1 and 606-2 (collectively "main current 606") may be applied to electrodes $E_{k-2}$ and $E_{k+1}$ concurrently with the application of main current 606-1 and 606-2 to electrodes $E_{k-1}$ and $E_k$. As shown, electrodes $E_{k-2}$ and $E_{k+1}$ surround electrodes $E_{k-1}$ and $E_k$. Compensating current 610 serves to focus the excitation field associated with the peak envelope, as represented by envelope 612. It will be recognized that compensating current may be applied by way of any number of compensating electrodes.

In some examples, compensating current 610 is less than main current 606. In these examples, a remaining amount of current equal to the difference between main current 606 and compensating current 610 flows to an extracochlear ground electrode, as will be described below. Alternatively, compensating current 610 may be substantially equal in amplitude to main current 606.

As mentioned, control facility 304 may be configured to use relatively more focusing with respect to low frequency analysis channels below the crossover frequency than with respect to high frequency analysis channels above the crossover frequency. This may be performed in any suitable manner.

For example, with respect to a particular low frequency analysis channel, control facility 304 may direct cochlear implant 108 to apply main current to at least one main electrode associated with the low frequency analysis channel to represent a frequency domain signal contained within the low frequency analysis channel and compensating current to two or more compensating electrodes associated with the low frequency analysis channel to focus the excitation field created by the main current, as described in connection with FIG. 6. Likewise, with respect to a particular high frequency analysis channel, control facility 304 may direct cochlear implant 108 to apply main current to at least one main electrode associated with the high frequency analysis channel to represent a frequency domain signal contained within the high frequency analysis channel and compensating current to two or more compensating electrodes associated with the high frequency analysis channel to focus the excitation field created by the main current, as described in connection with FIG. 6. In this scenario, control facility 304 may use relatively more focusing with respect to the low frequency analysis channel than with respect to the high frequency analysis channel by directing cochlear implant 108 to apply relatively less compensating current to the compensating electrodes associated with the high frequency analysis channel than to the compensating electrodes associated with the low frequency analysis channel.

Additionally or alternatively, control facility 304 may use relatively more focusing with respect to the low frequency analysis channel than with respect to high frequency analysis channel by ensuring that the total number of compensating electrodes used with respect to the high frequency analysis channel is fewer than the total number of compensating electrodes used with respect to the low frequency analysis channel. For example, compensating current may be applied to four or more compensating electrodes associated with the low frequency analysis channel while compensating current may be applied to only two compensating electrodes associated with the high frequency analysis channel.

Additionally or alternatively, control facility 304 may use relatively more focusing with respect to the low frequency analysis channel than with respect to high frequency analysis channel by directing cochlear implant 108 to abstain from applying compensating current in connection with the high frequency analysis channel. In this manner, no focusing is performed with respect to the high frequency analysis channel.

In some examples, the degree of focusing used for each low frequency analysis channel included in a plurality of low frequency analysis channels depends on a spectral distance of each low frequency analysis channel from the crossover frequency. For example, the degree of focusing may gradually increase the further away a low frequency analysis channel is from the crossover frequency. To illustrate, with reference to FIG. 4, relatively more focusing may be used for low frequency analysis channel 404-1 than for low frequency analysis channel 404-5 because low frequency analysis channel 404-1 is further away from the crossover frequency than low frequency analysis channel 404-5.

In some examples, the high frequency stimulation strategy used to represent frequency domain signals in the high frequency analysis channels is a fixed current steering strategy that does not include any degree of focusing. As used herein, a "fixed current steering strategy" is one that fixes the weighting of main current applied to each main electrode such that the same amount of current is applied to each main electrode. For example, a fixed current steering strategy may direct cochlear implant 108 to apply equally weighted stimulation current to two main electrodes. In this manner, the amplitude of the stimulation current applied to each main electrode is fifty percent of the maximum possible amplitude, thereby conserving power. A fixed current steering strategy that does not include any degree of focusing is one that does not apply compensating current together with the main current.

Figure 7:
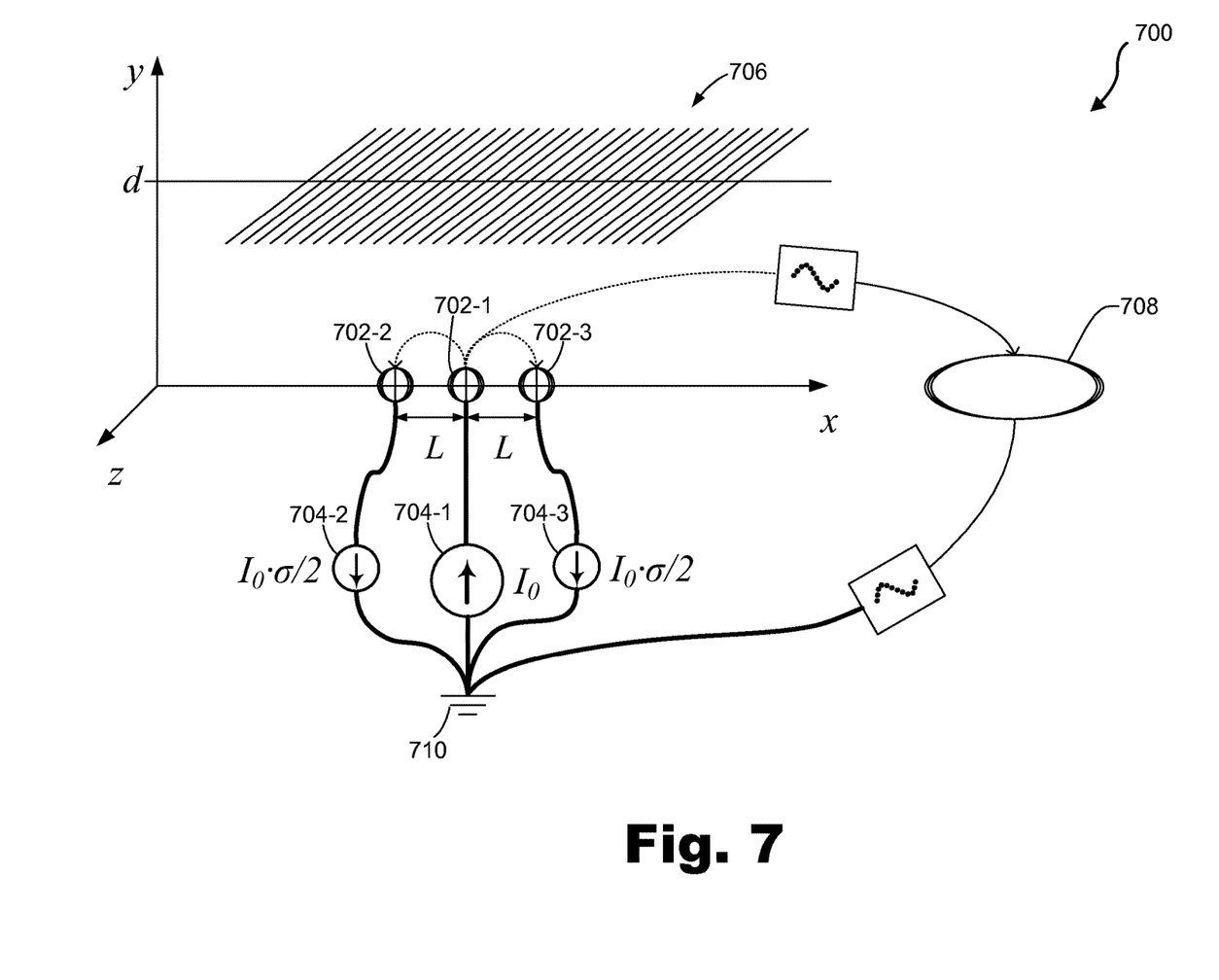
FIG. 7 shows an exemplary electrode arrangement that may be used to selectively operate in one of a monopolar stimulation configuration, a full multipolar stimulation configuration, and a partial multipolar stimulation configuration according to principles described herein.

Various types of non-focusing stimulation strategies (i.e., stimulation strategies that do not include focusing) and focusing stimulation strategies (i.e., stimulation strategies that include focusing) that may be used by control facility 304 will now be described in connection with FIG. 7. FIG. 7 shows an exemplary electrode arrangement 700 that may be used to selectively operate in one of a monopolar stimulation configuration, a full multipolar stimulation configuration, and a partial multipolar stimulation configuration.

As used herein, a "monopolar stimulation configuration" refers to a non-focusing stimulation strategy in which stimulation current is passed through a single intracochlear electrode (i.e., an electrode that is implanted within the cochlea) and an extracochlear ground electrode (i.e., an electrode located outside the cochlea). In monopolar stimulation, all of the current flows between the intracochlear electrode and the extracochlear ground electrode.

As used herein, a "full multipolar stimulation configuration" refers to a non-focusing stimulation strategy in which stimulation current is simultaneously applied to a main intracochlear electrode and one or more intracochlear compensating electrodes without any of the stimulation current flowing to the extracochlear electrode. Hence, all of the current flows between the main intracochlear electrode and the one or more intracochlear compensating electrodes. Exemplary full multipolar stimulation configurations include, but are not limited to, full bipolar stimulation (where stimulation current is passed between two intracochlear electrodes) and full tripolar stimulation (where stimulation current is passed between three intracochlear electrodes).

As used herein, a "partial multipolar stimulation configuration" refers to a focusing stimulation strategy in which stimulation current is applied to a main intracochlear electrode while compensating current opposite in phase to that of the stimulation current is simultaneously applied to one or more intracochlear compensating electrodes. In partial multipolar stimulation, the total amount of compensating current applied to the compensating electrodes is less than the total amount of stimulation current applied to the main electrode. The remaining amount of current flows to the extracochlear ground electrode. For example, as will be described in more detail below, the amount of stimulation current applied to the main electrode may be represented by $I_0$ and the amount of stimulation current applied to the compensating electrodes may be represented by $\sigma I_0$ (i.e., $\sigma$ multiplied by $I_0$), where $\sigma$ is greater than zero and less than one. Hence, the remaining amount of current that flows to the extracochlear ground electrode may be represented by $(1-\sigma)*I_0$.

As shown in FIG. 7, electrode arrangement 700 may include a main intracochlear electrode 702-1 and a plurality of compensating intracochlear electrodes (e.g., electrodes 702-2 and 702-3) surrounding main electrode 702-1. Electrodes 702-1 through 702-3 will be collectively referred to herein as "electrodes 702". An independent current source 704 (e.g., current sources 704-1 through 704-3) may correspond to each electrode 702. Current sources 704 may be included within cochlear implant 108, for example, and may be configured to generate the stimulation current that is applied to each electrode 702.

In some examples, electrodes 702 are collinearly positioned a certain distance d away from a stimulation site 706 (e.g., the auditory nerve). For example, the electrodes 702 shown in FIG. 7 are collinearly located along a particular axis (e.g., the x-axis). Moreover, as shown in FIG. 7, the electrodes 702 may be separated one from another by a separation distance L. The separation distance L and the distance d may vary as may serve a particular application. It will also be recognized that electrodes 702 may be positioned in any alternative arrangement as may serve a particular application. For example, the electrodes 702 may be located within different planes.

Three intracochlear electrodes 702 are shown in FIG. 7 for illustrative purposes. The three intracochlear electrodes 702 may be configured to selectively operate in one of a monopolar stimulation configuration, a full tripolar stimulation configuration, and a partial tripolar stimulation configuration. It will be recognized that any other number of intracochlear electrodes 702 may be included within electrode configuration 700 in order to realize other types of full and/or partial multipolar stimulation. For example, two intracochlear electrodes 702 may be used to realize full and/or partial bipolar stimulation and/or four intracochlear electrodes 702 may be used to realize full and/or partial quadrapolar stimulation.

Electrode arrangement 700 may further include an extracochlear ground electrode 708 and a circuit ground 710. Extracochlear ground electrode 708 may be implemented using the case of cochlear implant 108, disposed on a proximal portion of a lead that is inserted into the cochlea, and/or otherwise implemented in any suitable manner. Circuit ground 710 may include a ground trace, for example, disposed within cochlear implant 108. In some examples, a portion of the stimulation current applied to electrodes 702-1 may be returned to circuit ground 710 by way of extracochlear ground electrode 708 when electrodes 702 are configured to operate in a partial multipolar stimulation configuration.

Stimulation current may be selectively and simultaneously applied to one or more of electrodes 702-1 by one or more of current sources 704 in order to realize monopolar stimulation, full multipolar stimulation, and/or partial multipolar stimulation. To illustrate, FIG. 7 shows that a stimulation current $I_0$ may be applied to main electrode 702-1. The stimulation current $I_0$ may be generated by cochlear implant 108, for example, in accordance with one or more stimulation parameters provided by sound processor 104 as may serve a particular application.

Current may also be applied to compensating electrodes 702-2 and 702-3 in order to focus or narrow the excitation field caused by main electrode 702-1. The compensating current is opposite in phase as the stimulation current $I_0$ and may be represented by $I_0*\sigma/2$, wherein a represents a programmable multiplication factor or "focusing factor" ranging from 0 to 1. Hence, the total compensating current applied to compensating electrodes 702-2 and 702-3 may be varied from 0 to $I_0$. By so doing, stimulation current may be selectively applied to stimulation site 706 in a monopolar stimulation configuration, a full multipolar stimulation configuration, or a partial multipolar stimulation configuration.

To illustrate, a monopolar stimulation configuration may be realized by adjusting the focusing factor σ to equal 0 in order to prevent current from being applied to compensating electrodes 702-2 and 702-3. In this manner, stimulation current is only applied to main electrode 702-1, thereby resulting in a monopolar stimulation configuration.

Alternatively, a full multipolar stimulation configuration may be realized by adjusting the focusing factor σ to equal 1 in order to apply an equal amount of current via compensating electrodes 702-2 and 702-3 as is applied via the main electrode 702-1. In such a configuration, compensating current equal $I_0/2$ is applied to each of the compensating electrodes 702-2 and 702-3 shown in FIG. 7. Because the total amount of compensating current applied to compensating electrodes 702-2 and 702-3 is equal to the amount of current applied to main electrode 702-1, no current passes through extracochlear ground electrode 708 in full multipolar stimulation configuration.

A partial multipolar stimulation configuration may be realized by adjusting the focusing factor σ to a value in between, but not including, 0 and 1 such that the total amount of current applied by compensating electrodes 702-2 and 702-3 is greater than 0 and less than $I_0$. In such a stimulation configuration, an amount of current equal to $(1-\sigma)*I_0$ returns to circuit ground 710 by way of extracochlear ground electrode 708. For example, if focusing factor σ is equal to 0.5, half of stimulation current $I_0$ flows through compensating electrodes 702-2 and 702-3 to circuit ground 710 and half of stimulation current $I_0$ flows through extracochlear ground electrode 708 to circuit ground 710.

Compensating electrodes 702-2 and 702-3 shown in FIG. 7 are both configured to apply an equal amount of compensating current (i.e., $I_0*\sigma/2$) for illustrative purposes only. It will be recognized that compensating electrodes 702-2 and 702-3 may alternatively be configured to apply different amounts of compensating current as may serve a particular application.

As described above, current steering may be used in connection with the stimulation strategies described herein. In current steering, weighted stimulation current is applied concurrently to two or more electrodes by a cochlear implant in order to stimulate a stimulation site located in between areas associated with the two or more electrodes and thereby create a perception of a frequency in between the frequencies associated with the two or more electrodes.

Figure 8:
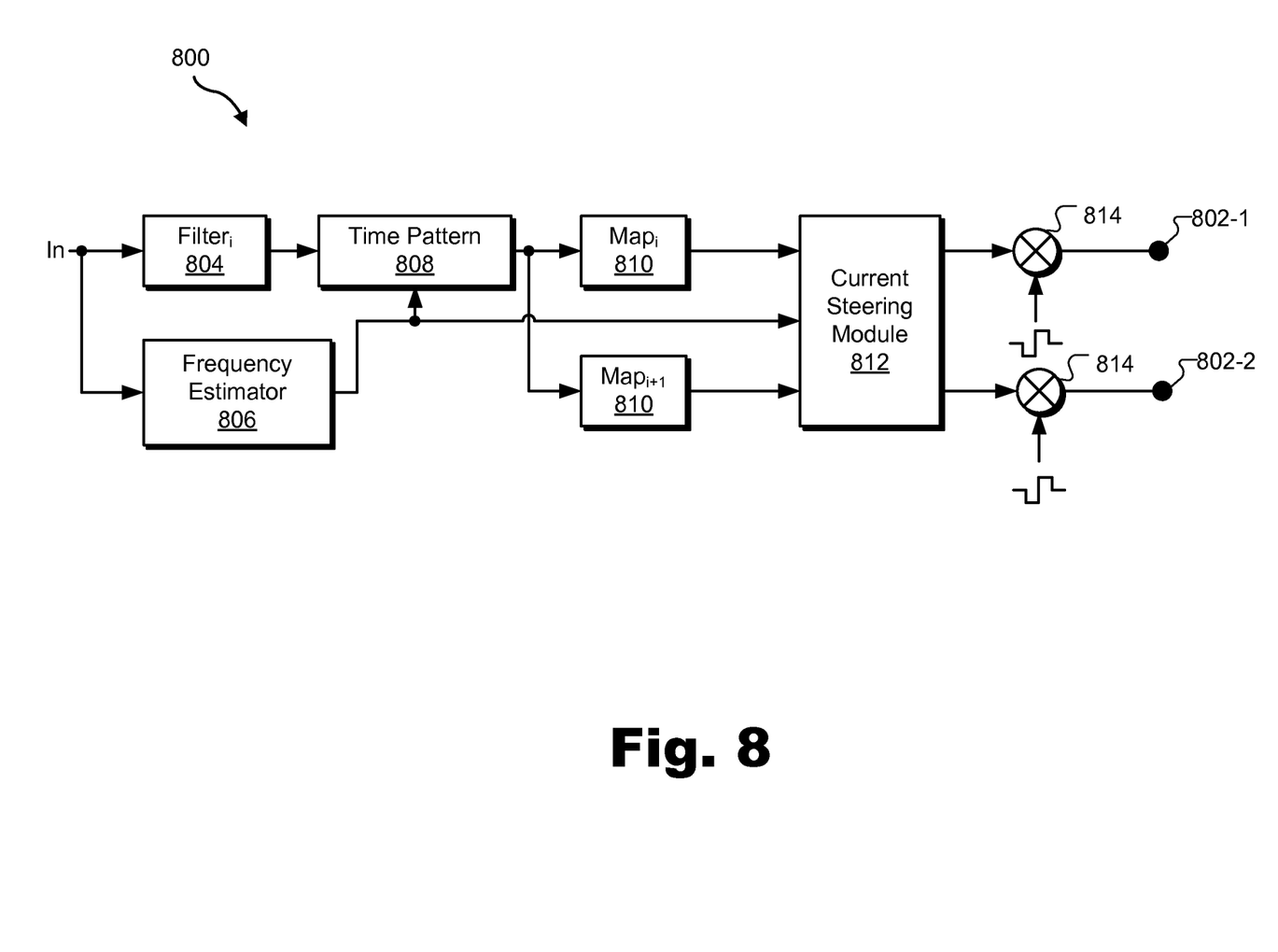
FIG. 8 illustrates an exemplary implementation of a current steering strategy according to principles described herein.

FIG. 8 illustrates an exemplary implementation 800 of a current steering strategy. The components and functions illustrated in FIG. 8 may be implemented by any of the subsystems, facilities, and/or modules described herein. For example, one or more components of sound processor 104 may be configured to perform any of the functions described in connection with FIG. 8.

As shown in FIG. 8, current steering may be applied to two or more electrodes 802 (e.g., electrodes 802-1 and 802-2). Two electrodes 802 are shown in FIG. 8 for illustrative purposes only. It will be recognized that current steering may alternatively be applied to three or more electrodes as may serve a particular application. Electrodes 802-1 and 802-2 may be adjacent one to another (i.e., no other electrode 802 is physically disposed in between them on a lead). Alternatively, electrodes 802-1 and 802-2 may be non-adjacent (i.e., one or more electrodes 802 are physically disposed in between them on a lead).

As shown in FIG. 8, an input signal may be filtered by at least one filter 804 configured to generate a frequency domain signal representative of a distinct frequency portion of the audio signal. The input signal is also input into a frequency estimator 806 configured to estimate the peak frequency thereof. A time pattern block 808 is configured to build the temporal structure of a pulse train representing the signal output by the at least one filter 804. Mapping modules 810 are configured to map the amplitude of the signal output by the time pattern block 808 to corresponding current levels in accordance with a suitable mapping function.

The output of each mapping module 810 is input into a current steering module 812. The current steering module 812 is also configured to receive the output of the frequency estimator 806. In some examples, the current steering module 812 is configured to determine appropriate weighting factors for current to be applied to electrodes 802-1 and 802-2. This determination may be based at least in part on the peak frequency estimate and the output of each of the mapping modules 810. The weighting factors may be applied to the current using multiplication blocks 814. In this manner, stimulation current may be delivered to a stimulation site located in between areas associated with electrodes 802-1 and 802-2.

Figure 9:
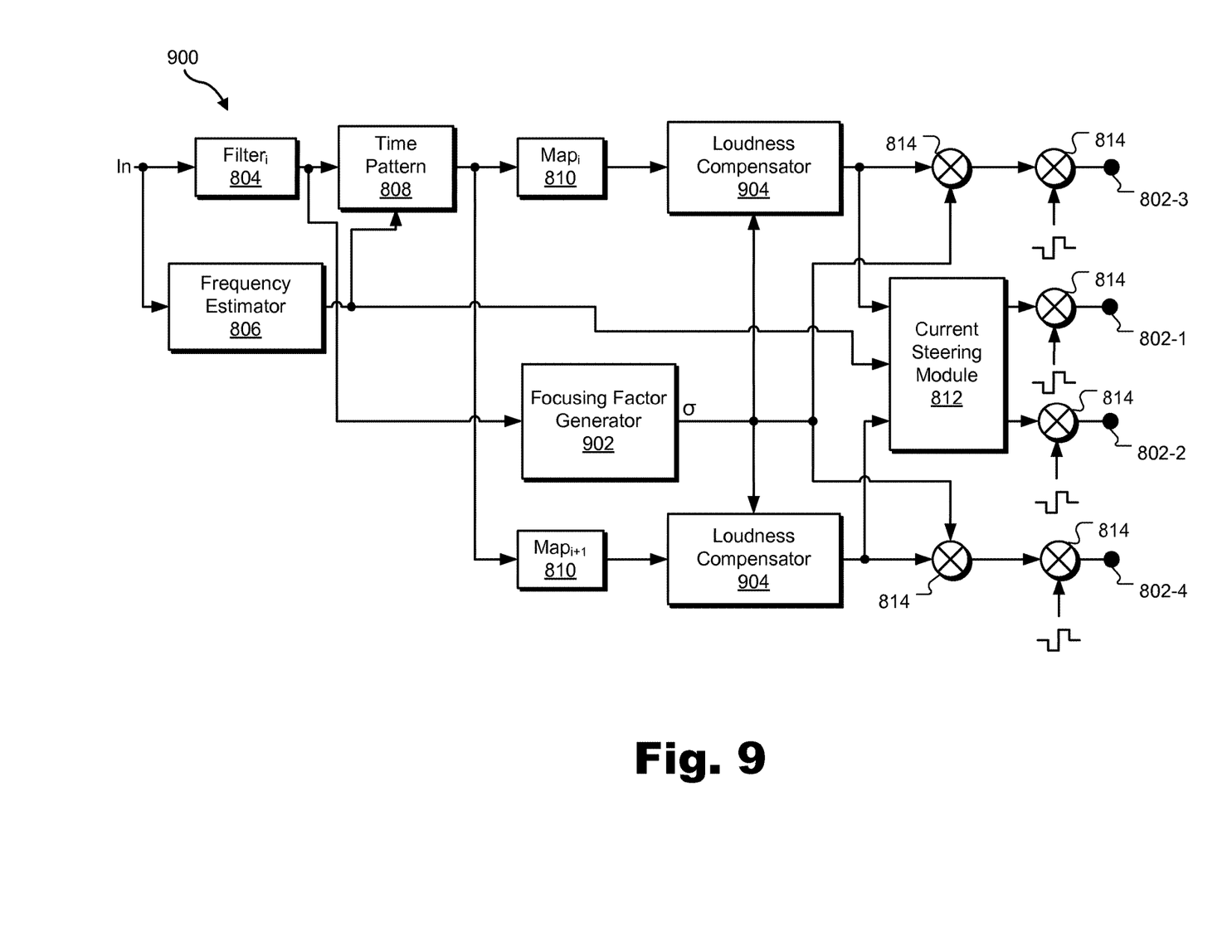
FIG. 9 illustrates an exemplary implementation of a current steering strategy that may be used to dynamically focus one or more excitation fields produced by current steering electrodes according to principles described herein.

The excitation field produced by the current steering electrodes 802-1 and 802-2 may be focused by applying compensating current simultaneously to one or more additional electrodes (referred to herein as compensating electrodes). To illustrate, FIG. 9 illustrates another exemplary implementation 900 of a current steering strategy that may be used to dynamically focus one or more excitation fields produced by current steering electrodes (e.g., electrodes 802-1 and 802-2). The components and functions illustrated in FIG. 9 may be implemented by any of the subsystems, facilities, and/or modules described herein. For example, one or more components of sound processor 104 may be configured to perform any of the functions described in connection with FIG. 9.

Implementation 900 includes many of the same components as the implementation described in connection with FIG. 8. In addition, functional block diagram 900 includes a focusing factor generator 902 configured to generate focusing factor σ based on the amplitude of the signal output by filter 804. The focusing factor σ is used to generate scaled versions of the current steering current. This scaled current is delivered via one or more additional electrodes (e.g., electrodes 802-3 and 802-4) to effectively focus or narrow the excitation field produced by electrodes 802-1 and 802-2.

As shown in FIG. 9, loudness compensators 904 may also be included within the implementation 900 of FIG. 9. Loudness compensators 904 are configured to adjust the amplitudes of the currents applied via electrodes 802-1 and 802-2 to compensate for loudness changes that may be caused by current delivered via the compensating electrodes 802-3 and 802-4.

While exemplary implementations 800 and 900 of a current steering stimulation strategy have been described herein, it will be recognized that other implementations of a current steering stimulation strategy may be additionally or alternatively used as may serve a particular implementation.

Figure 10:
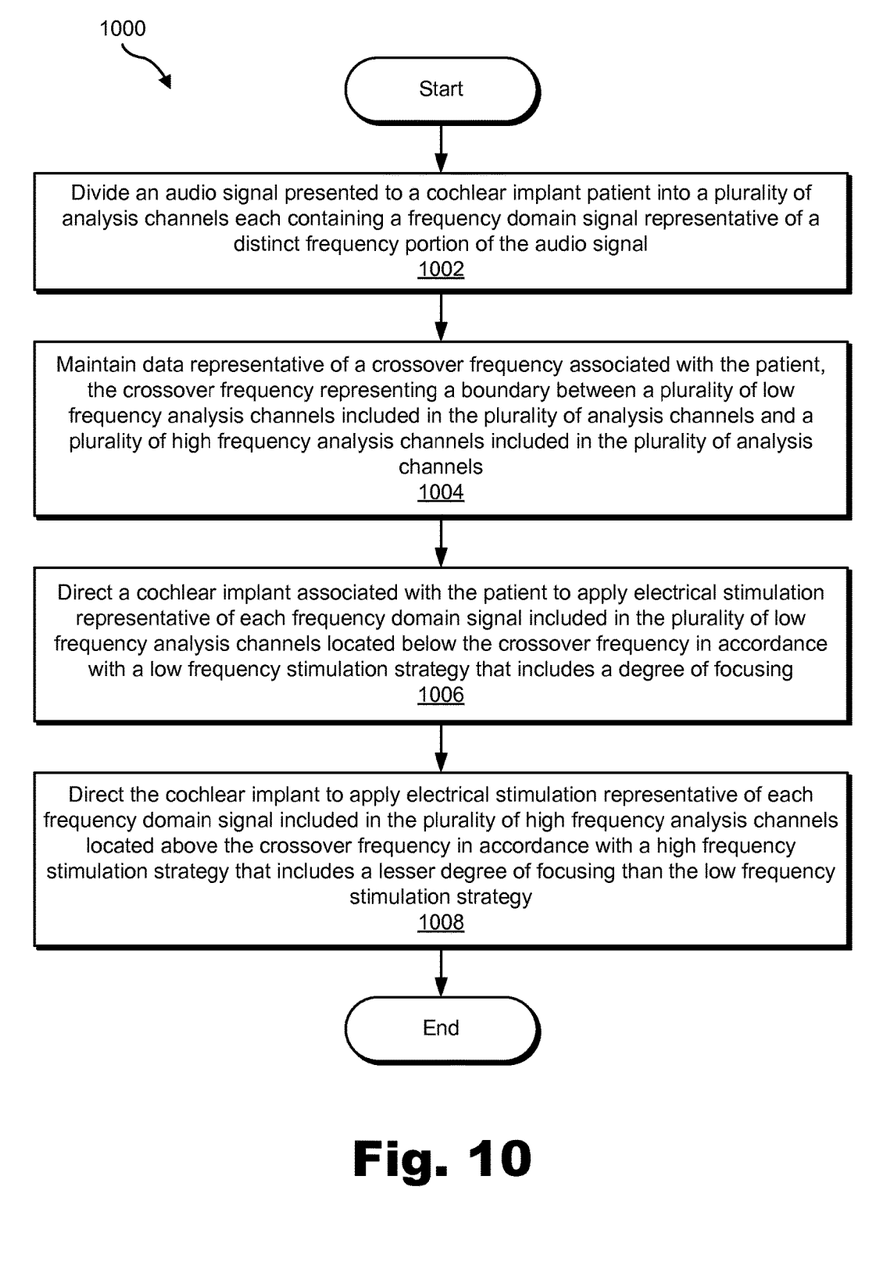
FIG. 10 illustrates an exemplary frequency-dependent focusing method according to principles described herein.

FIG. 10 illustrates an exemplary frequency-dependent focusing method 1000 for use in a cochlear implant system. While FIG. 10 illustrates exemplary steps according to one embodiment, other embodiments may omit, add to, reorder, and/or modify any of the steps shown in FIG. 10. One or more of the steps shown in FIG. 10 may be performed by sound processor 104 and/or any implementation thereof.

In step 1002, a sound processor divides an audio signal presented to a cochlear implant patient into a plurality of analysis channels each containing a frequency domain signal representative of a distinct frequency portion of the audio signal. Step 1002 may be performed in any of the ways described herein.

In step 1004, the sound processor maintains data representative of a crossover frequency associated with the patient. As described above, the crossover frequency represents a boundary between a plurality of low frequency analysis channels included in the plurality of analysis channels and a plurality of high frequency analysis channels included in the plurality of analysis channels. Step 1004 may be performed in any of the ways described herein.

In step 1006, the sound processor directs a cochlear implant associated with the patient to apply electrical stimulation representative of each frequency domain signal included in the plurality of low frequency analysis channels located below the crossover frequency in accordance with a low frequency stimulation strategy that includes a degree of focusing. Step 1006 may be performed in any of the ways described herein.

In step 1008, the sound processor directs the cochlear implant to apply electrical stimulation representative of each frequency domain signal included in the plurality of high frequency analysis channels located above the crossover frequency in accordance with a high frequency stimulation strategy that includes a lesser degree of focusing than the low frequency stimulation strategy. Step 1008 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a processing facility configured to
divide an audio signal presented to a cochlear implant patient into a plurality of analysis channels each containing a frequency domain signal representative of a distinct frequency portion of the audio signal, and
maintain data representative of a crossover frequency associated with the patient, the crossover frequency representing a boundary between a plurality of low frequency analysis channels included in the plurality of analysis channels and a plurality of high frequency analysis channels included in the plurality of analysis channels; and
a control facility communicatively coupled to the processing facility and that is configured to
direct a cochlear implant associated with the patient to apply electrical stimulation representative of each frequency domain signal included in the plurality of low frequency analysis channels located below the crossover frequency in accordance with a low frequency stimulation strategy that includes a degree of focusing, and
direct the cochlear implant to apply electrical stimulation representative of each frequency domain signal included in the plurality of high frequency analysis channels located above the crossover frequency in accordance with a high frequency stimulation strategy that includes a lesser degree of focusing than the low frequency stimulation strategy.

2. The system of claim 1, wherein the processing facility is further configured to determine the crossover frequency in accordance with a fitting procedure performed with respect to the patient.

3. The system of claim 1, wherein the processing facility is further configured to:
classify the audio signal; and
determine the crossover frequency based on the classification of the audio signal.

4. The system of claim 1, wherein the control facility is configured to direct the cochlear implant to apply electrical stimulation representative of a frequency domain signal included in a particular low frequency analysis channel included in the plurality of low frequency analysis channels in accordance with the low frequency stimulation strategy by directing the cochlear implant to concurrently:
apply a main current to at least one main electrode associated with the particular low frequency analysis channel; and
apply a compensating current to two or more compensating electrodes associated with the particular low frequency analysis channel;
wherein the compensating current is opposite in polarity compared to the main current.

5. The system of claim 4, wherein the two or more compensating electrodes include at least a first compensating electrode and a second compensating electrode that surround the at least one main electrode.

6. The system of claim 4, wherein the compensating current is less than the main current and wherein a remaining amount of current equal to the difference between the main current and the compensating current flows to an extracochlear ground electrode.

7. The system of claim 4, wherein the compensating current is substantially equal to the main current.

8. The system of claim 4, wherein the at least one main electrode comprises a first main electrode and a second main electrode adjacent one to another, and wherein the control facility is configured to direct the cochlear implant to apply the main current to the at least one main electrode by directing the cochlear implant to concurrently apply a first weighted portion of the main current to the first main electrode and a second weighted portion of the main current to the second main electrode in accordance with a current steering strategy.

9. The system of claim 4, wherein the control facility is configured to direct the cochlear implant to apply electrical stimulation representative of a frequency domain signal included in a particular high frequency analysis channel included in the plurality of high frequency analysis channels in accordance with the high frequency stimulation strategy by directing the cochlear implant to concurrently:

apply a main current to at least one main electrode associated with the particular high frequency analysis channel; and apply a compensating current to two or more compensating electrodes associated with the particular high frequency analysis channel;

wherein the compensating current applied to the two or more compensating electrodes associated with the particular high frequency analysis channel is opposite in polarity compared to the main current applied to the at least one main electrode associated with the particular high frequency analysis channel.

10. The system of claim 9, wherein the compensating current applied to the two or more compensating electrodes associated with the particular high frequency analysis channel is less than the compensating current applied to the two or more compensating electrodes associated with the particular low frequency analysis channel such that a degree of focusing performed with respect to the particular high frequency analysis channel is less than a degree of focusing performed with respect to the particular low frequency analysis channel.

11. The system of claim 9, wherein a total number of electrodes included in the two or more additional compensating electrodes associated with the particular high frequency analysis channel is less than a total number of electrodes included in the two or more compensating electrodes associated with the particular low frequency analysis channel such that a degree of focusing performed with respect to the particular high frequency analysis channel is less than a degree of focusing performed with respect to the particular low frequency analysis channel.

12. The system of claim 4, wherein the control facility is configured to direct the cochlear implant to apply electrical stimulation representative of a frequency domain signal included in a particular high frequency analysis channel included in the plurality of high frequency analysis channels in accordance with the high frequency stimulation strategy by directing the cochlear implant to:

apply a main current to at least one main electrode associated with the particular high frequency analysis channel; and abstain from applying a compensating current associated with the particular high frequency analysis channel such that no focusing is performed with respect to the particular high frequency analysis channel.

13. The system of claim 12, wherein the at least one main electrode associated with the particular high frequency analysis channel comprises a plurality of electrodes adjacent one to another, and wherein the control facility is configured to direct the cochlear implant to apply the main current to the at least one main electrode associated with the particular high frequency analysis channel by directing the cochlear implant to concurrently apply the main current to the plurality of electrodes in accordance with a fixed current steering strategy.

14. The system of claim 1, wherein the control facility is configured to direct the cochlear implant to apply the electrical stimulation representative of each frequency domain signal included in the plurality of high frequency analysis channels located above the crossover frequency in accordance with the high frequency stimulation strategy by preventing the cochlear implant from applying compensating current to one or more compensating electrodes while the electrical stimulation representative of each frequency domain signal included in the plurality of high frequency analysis channels is applied such that no focusing is performed with respect to any of the high frequency analysis channels.

15. The system of claim 1, wherein the high frequency stimulation strategy is a fixed current steering strategy that does not include any degree of focusing.

16. The system of claim 1, wherein the degree of focusing included in the low frequency stimulation strategy is dependent on a spectral distance of each low frequency analysis channel included in the plurality of low frequency analysis channels from the crossover frequency.

17. A method comprising:

dividing, by a sound processor, an audio signal presented to a cochlear implant patient into a plurality of analysis channels each containing a frequency domain signal representative of a distinct frequency portion of the audio signal;

maintaining, by the sound processor, data representative of a crossover frequency associated with the patient, the crossover frequency representing a boundary between a plurality of low frequency analysis channels included in the plurality of analysis channels and a plurality of high frequency analysis channels included in the plurality of analysis channels;

directing, by the sound processor, a cochlear implant associated with the patient to apply electrical stimulation representative of each frequency domain signal included in the plurality of low frequency analysis channels located below the crossover frequency in accordance with a low frequency stimulation strategy that includes a degree of focusing; and directing, by the sound processor, the cochlear implant to apply electrical stimulation representative of each frequency domain signal included in the plurality of high frequency analysis channels located above the crossover frequency in accordance with a high frequency stimulation strategy that includes a lesser degree of focusing than the low frequency stimulation strategy.

18. The method of claim 17, wherein the directing of the cochlear implant to apply electrical stimulation representative of a frequency domain signal included in a particular low frequency analysis channel included in the plurality of low frequency analysis channels in accordance with the low frequency stimulation strategy comprises directing the cochlear implant to concurrently:

apply a main current to at least one main electrode associated with the particular low frequency analysis channel; and apply a compensating current to two or more compensating electrodes associated with the particular low frequency analysis channel;

wherein the compensating current is opposite in polarity compared to the main current.

19. The method of claim 17, wherein the high frequency stimulation strategy is a fixed current steering strategy that does not include any degree of focusing.

* * * * *